United States Patent [19]

Shvetsky

[11] Patent Number: 5,942,690
[45] Date of Patent: Aug. 24, 1999

[54] APPARATUS AND METHOD FOR ULTRASONIC INSPECTION OF ROTATING MACHINERY WHILE THE MACHINERY IS IN OPERATION

[76] Inventor: Arkady Shvetsky, 3601 Parkview La., Apt. 24D, Irvine, Calif. 92715

[21] Appl. No.: 08/977,036

[22] Filed: Nov. 25, 1997

[51] Int. Cl.⁶ .......................... G01N 29/10; G01N 29/24
[52] U.S. Cl. ................... 73/660; 73/659; 73/593
[58] Field of Search .................... 73/660, 659, 650, 73/627, 628, 629, 630, 620, 603, 602, 593, 865.8, 609, 616; 29/889.2, 889.21, 889.23

[56] References Cited

U.S. PATENT DOCUMENTS

| | | | |
|---|---|---|---|
| 3,336,794 | 8/1967 | Wysoczanski et al. | 73/600 |
| 3,400,578 | 9/1968 | Frarey et al. | 73/116 |
| 3,572,936 | 3/1971 | Johnson et al. | 356/348 |
| 3,608,363 | 9/1971 | Whittington | 73/609 |
| 3,763,698 | 10/1973 | Suzuki et al. | 73/778 |
| 3,952,566 | 4/1976 | Jacobson | 73/593 |
| 3,969,926 | 7/1976 | Walker et al. | 73/620 |
| 4,064,742 | 12/1977 | Pittaro | 73/611 |
| 4,089,225 | 5/1978 | Kraska et al. | 73/614 |
| 4,246,800 | 1/1981 | Bidgood et al. | 73/861.27 |
| 4,275,589 | 6/1981 | Dugger et al. | 73/146 |
| 4,334,431 | 6/1982 | Kohno et al. | 73/597 |
| 4,422,333 | 12/1983 | Leon | 73/660 |
| 4,531,408 | 7/1985 | Chadwick et al. | 73/455 |
| 4,566,225 | 1/1986 | Bizot et al. | 51/165.72 |
| 4,733,963 | 3/1988 | Date et al. | 356/35 |
| 4,788,866 | 12/1988 | Tanimoto et al. | 73/606 |
| 4,809,184 | 2/1989 | O'Donnell et al. | 364/413.25 |
| 4,936,138 | 6/1990 | Cushman et al. | 73/146 |
| 4,988,979 | 1/1991 | Sasaki et al. | 340/683 |
| 5,125,264 | 6/1992 | Beuzard et al. | 73/61.75 |
| 5,188,112 | 2/1993 | Sturgill et al. | 128/661.09 |
| 5,275,052 | 1/1994 | Luttrell et al. | 73/619 |
| 5,372,043 | 12/1994 | Speight, II et al. | 73/619 |
| 5,377,684 | 1/1995 | Hara | 128/661.09 |
| 5,410,405 | 4/1995 | Schultz et al. | 356/351 |
| 5,445,027 | 8/1995 | Zorner | 73/593 |
| 5,445,029 | 8/1995 | Falsetti et al. | 73/609 |
| 5,469,743 | 11/1995 | Zorn | 73/627 |
| 5,471,880 | 12/1995 | Lang et al. | 73/660 |
| 5,479,826 | 1/1996 | Twerdochlib et al. | 73/660 |
| 5,487,387 | 1/1996 | Trahey et al. | 128/660.02 |

OTHER PUBLICATIONS

American Society For Metals, *Metals Handbook*, vol. 11, Nondestructive Inspection and Quality Control, 8th Edition, 1976.

"Proceedings: EPRI Steam Turbine and Generator NDE, Life Assessment, and maintenance Workshop", Electric Power Research Institute, TR–101333, Project 3232–01, Proceedings Oct. 1992, pp. 2–1 through 2–17; 3–1 through 3–5;4–1 through 4–18; 5–1 through 5–7; 5–12; 6–2 through 6–25; 7–2 through 7–8.

"Nondestructive Examination of Steam Turbine Blades: An Assessment", Electric Power Research Institute, CS–3675, Project 1266–24, Final report Nov. 1984, pp. 7–11 through 7–16; 8–1.

*Primary Examiner*—Michael Brock
*Assistant Examiner*—Rose M. Miller
*Attorney, Agent, or Firm*—Knobbe, Martens, Olson & Bear, LLP

[57] ABSTRACT

An ultrasonic stroboscope is used to inspect an object rotating at a first frequency to determine if the rotating object has any defects. The ultrasonic stroboscope includes a first acoustic transducer spaced apart from the rotating object. The first transducer is configured to radiate ultrasonic energy at the rotating object at a second frequency. The second frequency is substantially related to a sub-harmonic of the first frequency so that the rotating object appears acoustically substantially still. A second acoustic transducer is used to sense a reflection of the ultrasonic energy from a defect in the rotating object. The second transducer translates the sensed reflection into at least one reflection signal. A user interface is coupled to the reflection signal.

25 Claims, 8 Drawing Sheets

APPARATUS AND METHOD FOR ULTRASONIC INSPECTION OF ROTATING MACHINERY WHILE THE MACHINERY IS IN OPERATION

FIELD OF THE INVENTION

This invention relates to ultrasonic testing of flaws in machinery. In particular, this invention relates to systems and methods for detecting flaws in rotating machinery using stroboscopic ultrasound.

DESCRIPTION OF THE RELATED ART

Turbines play a vital role in a modem economy. For example, turbines are used in such important applications as electrical power generation and jet engines. However, turbines often suffer from catastrophic failures resulting from flaws in the turbine blades or other turbine components. The flaws may have been initially present in the component, or may be the result of the high degree of stress the turbine experiences during operation. For example, massive power plant steam turbines, having rotors weighing upwards of 180 tons, typically have rotation speeds of 3,600 revolutions per minute (RPM). The turbine, and in particular the turbine blades, operate in an extremely adverse environment, including centrifugal forces, pressure drops on either side of the blades, and temperature stresses due to uneven temperature distribution. As a result, turbine blades may suffer from cracks or fractures, particularly at the turbine blade mounting interface with a turbine disk. In a catastrophic failure, a turbine blade may completely separate from the disk. When the separated turbine blade impacts adjacent turbine blades rotating at 3,600 RPM, the adjacent blades may also fracture and separate. Furthermore, adjacent turbine stages and the turbine cylinder are likely to suffer extensive damage as well.

Turbine failures are a primary cause of power plant outages. The subsequent months of downtime and the cost of repair can be extremely expensive. Thus, many attempts have been made to detect the turbine rotor flaws before actual failure occurs. Traditionally, detection of turbine rotor flaws is accomplished by periodically taking the turbine out of operation, disassembling the turbine, and subjecting the turbine components to a variety of inspection techniques. These inspection techniques include visual and static ultrasonic inspection. However, the resulting downtime, disassembly and reassembly are still exceedingly expensive. Furthermore, if a flaw develops between scheduled inspections, the turbine may suffer a catastrophic failure before the next inspection. Alternatively, no flaw may be present, and thus the periodic inspection may be an unnecessary expense.

Several approaches have been used in an attempt to overcome the deficiencies of the aforementioned traditional approach. These approaches, including visual inspection, monitoring turbine rotor vibration, monitoring acoustic emissions of the turbine, monitoring the turbine temperature, and monitoring the axial strain on the turbine shaft, suffer from a variety of shortcomings. Thus, the above approaches are often inconsistent and inaccurate, and fail to pinpoint the location and type of flaw. For example, the visual inspection of a turbine blade provides little information as to the type and location of an internal flaw. As a result, none of the above approaches have successfully supplanted the traditional approach of halting the turbine operation to perform a thorough inspection.

SUMMARY OF THE INVENTION

The present invention is directed to novel systems and methods for inspecting rotating machinery, such as power generation turbine moving blades and disks, while the machinery is in operation. Thus, the present invention permits the early detection of flaws in rotating equipment, thus significantly reducing the probability of unplanned shutdowns caused by turbine failures as well as the need for planned outages for inspection purposes, resulting in a tremendous savings in maintenance cost and time. These savings may further result in lower consumer utility bills when the present invention is used to inspect power generating equipment.

In addition to inspecting power plant turbines, the present invention may be used to inspect numerous other types of rotating equipment. By way of example, the present invention may be used to inspect rotating mill components, such as rollers and drives, railroad and automotive components, such as axles and wheels, and ship components, such as propellers and shafts. Furthermore, the present invention may be used to inspect the aforementioned components while the components are in operation.

In a preferred embodiment, an ultrasonic transducer is mounted on a turbine casing. The transducer radiates pulses of ultrasonic energy at a rotating turbine disk having at least one blade at a repetition frequency substantially related to the frequency of the turbine disk rotation. In a preferred embodiment, the transducer radiates pulses of ultrasonic energy at a repetition frequency substantially equal to the frequency or a sub-harmonic of the frequency of the turbine disk rotation. The blade is acoustically highlighted by the pulsed ultrasonic energy and thus will appear substantially stationary. The transducer senses reflections of the ultrasonic pulses and translates the sensed reflections into at least one electrical signal. The electrical signal is provided as an output for analysis.

DETAILED DESCRIPTION OF THE PREFERRED EMBODIMENTS

The present invention provides a system and method for the inspection of rotating equipment using a novel combination of ultrasonic and stroboscopic techniques.

In the prior art, ultrasonic sound waves have primarily been used for the non-destructive inspection of stationary, non-rotating, objects. Beams of high-frequency sound waves are typically coupled to the stationary object being inspected by placing a radiating source in direct contact with the stationary object. The sound waves then travel through the object until striking a discontinuity. When the sound waves strike the discontinuity, the waves are reflected back and produce an echo of the original sound waves. The reflected waves may then be detected and analyzed.

However, the above technique is completely inapplicable to the inspection of rotating equipment such as a rotating rotor in a gas turbine compressor ("turbocompressor"). The rotor 4, illustrated in FIG. 1A, has numerous blades around its periphery. While the generator is in operation, the turbocompressor rotor is rotating, and therefore it is not feasible to directly couple sound waves to the turbocompressor blades. Furthermore, if an ultrasonic pulse is directed at the rotating rotor 4, the pulse may end up striking any blade or the void between any two blades. Thus, using prior art techniques, it is not possible to determine the source of any reflected ultrasonic pulse to thereby determine if a defect exists in a given rotating blade. As a result, using prior art inspection methods, it is necessary to halt the operation of the generator before any ultrasonic inspection can take place.

One preferred embodiment of the present invention, as described below, uses novel and innovative systems and methods to overcome the aforementioned limitations of the prior art and provides the ability to ultrasonically inspect rotating equipment while in operation. In the preferred embodiment, an ultrasonic acoustic stroboscope permits inspection of a cyclically moving object in such a way as to produce an acoustic illusion of stopped or slowed motion. Thus, the cost and time required to inspect rotating equipment, such as turbocompressor rotors, are dramatically lowered. Furthermore, defects in the rotating equipment can be detected and corrected before a catastrophic failure occurs.

Figure 1A:
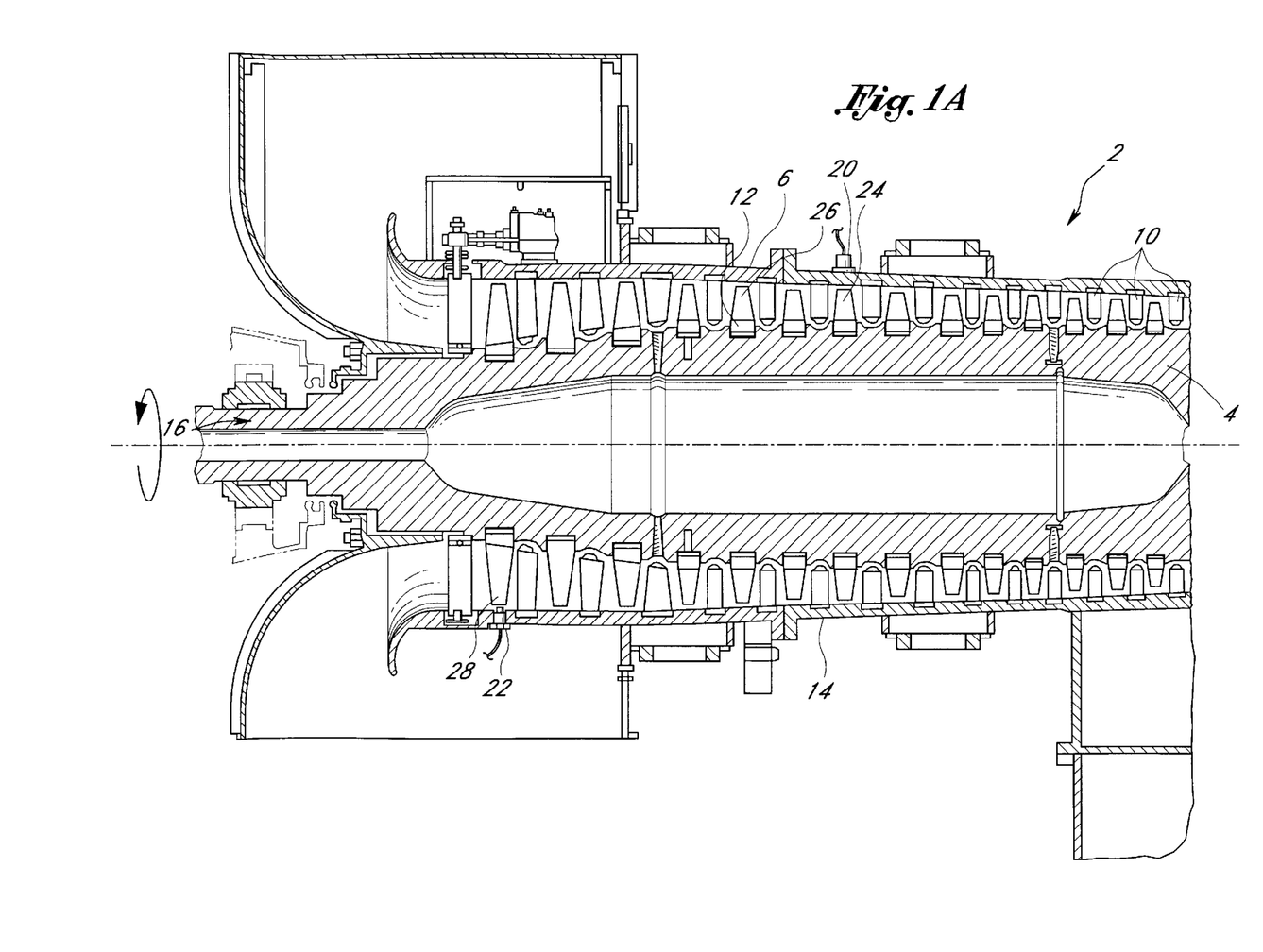
FIG. 1A illustrates a cross section of a gas turbine compressor including a preferred embodiment of the present invention.

FIG. 1A illustrates a preferred embodiment of a system for the stroboscopic ultrasonic inspection of an operating turbocompressor 2. The system may be used to detect physical flaws, such as cracks and fractures, in the turbocompressor rotating elements. The flaws may be manufacturing defects or the results of corrosion or stress.

The turbocompressor 2 includes a stationary portion 14 (the "stator"), and a movable portion (the "rotor") 4. The stator 14 includes a cylinder or casing 6 and stationary blades 10. The rotor includes a rotor shaft 16 and moving blades or tenons 24, 26, 28. The turbocompressor casing 6 may be made of carbon steel, while the blades 24, 26 may be made of a titanium alloy.

First and second acoustic transducers 20, 22 are mounted on the casing 6 and are spaced apart from the rotor 4. In one preferred embodiment, illustrated in FIG. 1A, each transducer 20, 22 acts as both a transmitter and receiver. Each transducer 20, 22 generates pulses of ultrasonic energy, which are radiated at corresponding blades rotating beneath the transducers 20, 22. As will be discussed below, the number of transducers used may vary from one to any number greater than one. Furthermore, the transducers may be optionally mounted using a variety of different techniques. For example, a transducer may be mounted using a bracket on the outside of the casing 6 as is the transducer 20, or through the casing 6 as is the transducer 22, or on the inside of the casing (not shown).

Mounting the transducer 20 on the outside of the turbocompressor casing 6 offers numerous advantages. First, the turbocompressor casing 6 does not have to be significantly modified or designed specifically to accept a transducer. Instead, the transducer may be mounted on an existing standard turbocompressor casing. Furthermore, by mounting the transducer 20 on the outside of the casing 6, additional transducers may be added as desired to increase the coverage of detection. In addition, rather than having numerous permanently mounted transducers to fully cover all desired observation regions, one or more removable externally mounted transducers may be used as follows. The transducer 20 is first mounted in a bracket (not shown) located over one turbocompressor stage, and measurements are taken. The transducer 20 is then moved to the next stage, and additional measurements are taken. The above steps are repeated until all stages have been inspected. Thus, utilizing a removable externally mounted transducer can greatly reduce the number of required transducers as well as their associated cost.

Mounting the transducer 22 through the turbocompressor casing 6 also has distinct advantages. Because the sensor portion of the transducer resides within the turbocompressor, transmitted and reflected pulses do not have to penetrate the turbocompressor casing 6. Thus, less attenuation of the transmitted pulses and corresponding reflected information occurs. In addition, having the transducer located at a fixed position minimizes the possibility of operator error in mounting the transducer.

In one preferred embodiment, the transducers 20, 22 are mounted over corresponding turbocompressor blades 24, 28. Thus, as the rotor 4 rotates, the turbocompressor blades 24, 28 will pass beneath the corresponding transducers 20, 22 once each revolution.

Figure 5:
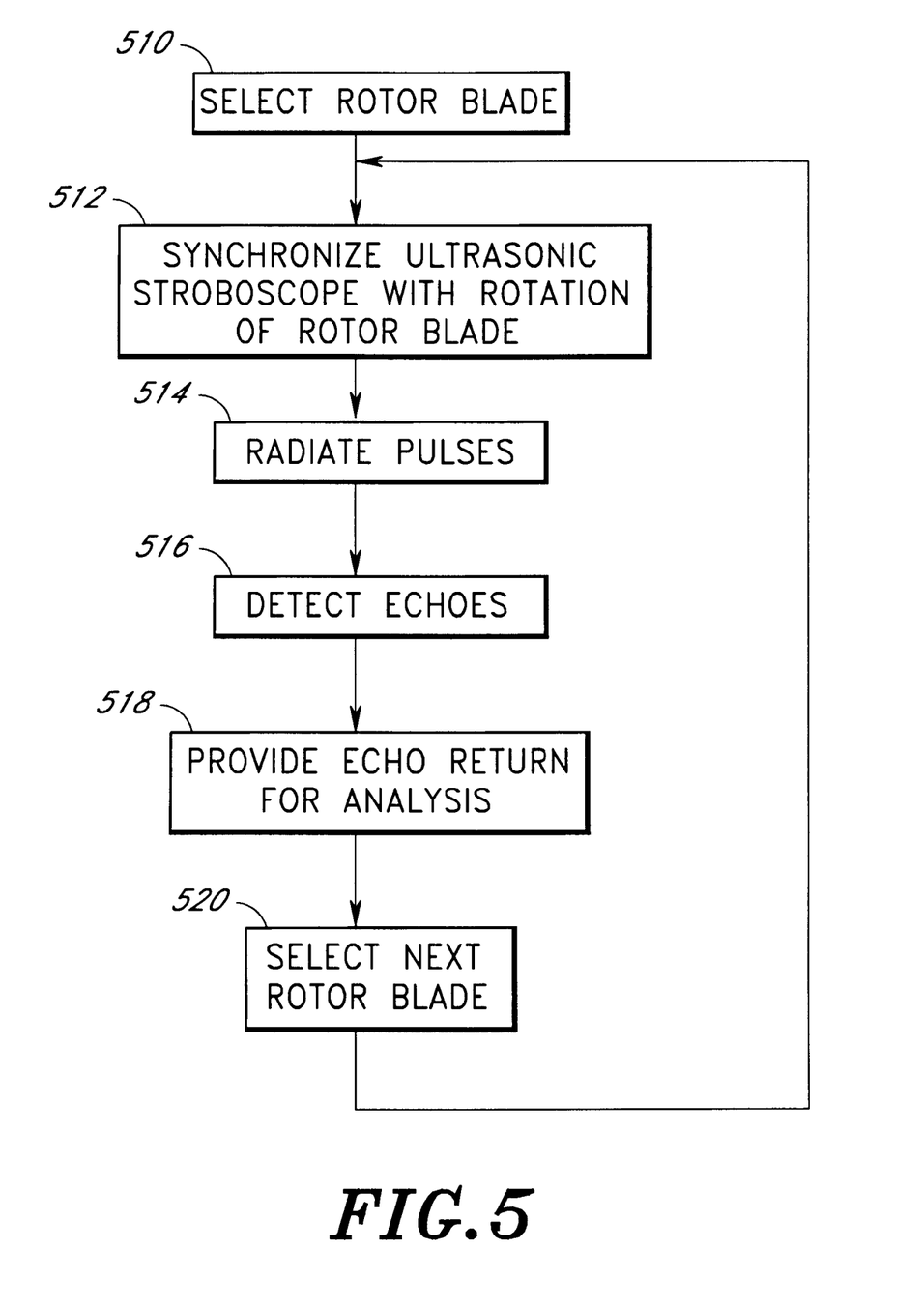
FIG. 5 illustrates a flow diagram of a preferred method of inspection.

As illustrated in FIGS. 1A and 5, in one embodiment, the present invention advantageously acts as an ultrasonic stroboscope. Each transducer 20, 22 radiates pulses of ultrasonic energy directed to a corresponding selected blade, as illustrated in FIG. 5, step 510. The pulses are generated at a repetition frequency substantially related to the frequency of the rotor rotation, thereby synchronizing the stroboscope with the rotor as illustrated in FIG. 5, step 512. Thus, the pulse repetition frequency may be selectively set at equal to a multiple or sub-harmonic of the rotation frequency. The term multiple as used herein includes fractional as well as integer multiples of the rotation frequency. Thus, by way of example, the repetition frequency may be set equal to the rotation frequency, or equal to one-half the rotation frequency, or equal to one-third the rotation frequency, and so on. For an electric generator used in the United States, the rotation frequency will be typically 3,600 revolutions per minute (RPM) which corresponds to a power line frequency of 60 Hz. For a electric generator used in Europe, or other localities having a line frequency of 50 Hz, the rotation frequency will be typically 3,000 RPM. In one embodiment, the pulses emitted by the transducers 20, 22 are further synchronized to the turbocompressor rotation using a periodic index signal related to the rotation frequency and provided by the turbocompressor. However, a index signal is not required for synchronization. For example in another embodiment, an operator synchronizes the pulses by observing the reflected return signals on a display and appropriately adjusting the frequency, width, and start times of the pulses.

Each time one of the blades 24, 28 rotates beneath a corresponding transducer 20, 22, the transducer emits one or more ultrasonic pulses so that the ultrasonic pulse strikes and highlights substantially only one corresponding blade (FIG. 5, step 514). When the pulse encounters a discontinuity, such a fracture or crack within a blade, at least a portion of the pulse is reflected back through the blade to the transducer.

In one preferred embodiment, the transducer receives at least a portion of the reflected ultrasonic pulses and translates the received reflections into at least one electrical signal, as illustrated in FIG. 5, step 516. The electrical signal is provided as an output for analysis as illustrated in FIG. 5, step 518. Thus, the pulsed ultrasonic wave, synchronized with the rotation of the rotor, causes a selected blade to appear substantially frozen or stationary. The pulsed ultrasonic wave will primarily travel in the "frozen" blade, rather than in any other blade. Thus, pulse echoes will advantageously be due to discontinuities in the "frozen" blade, rather than to discontinuities in any other blade. The process described above may be repeated for each rotor blade (FIG. 5, step 520).

Figure 7:
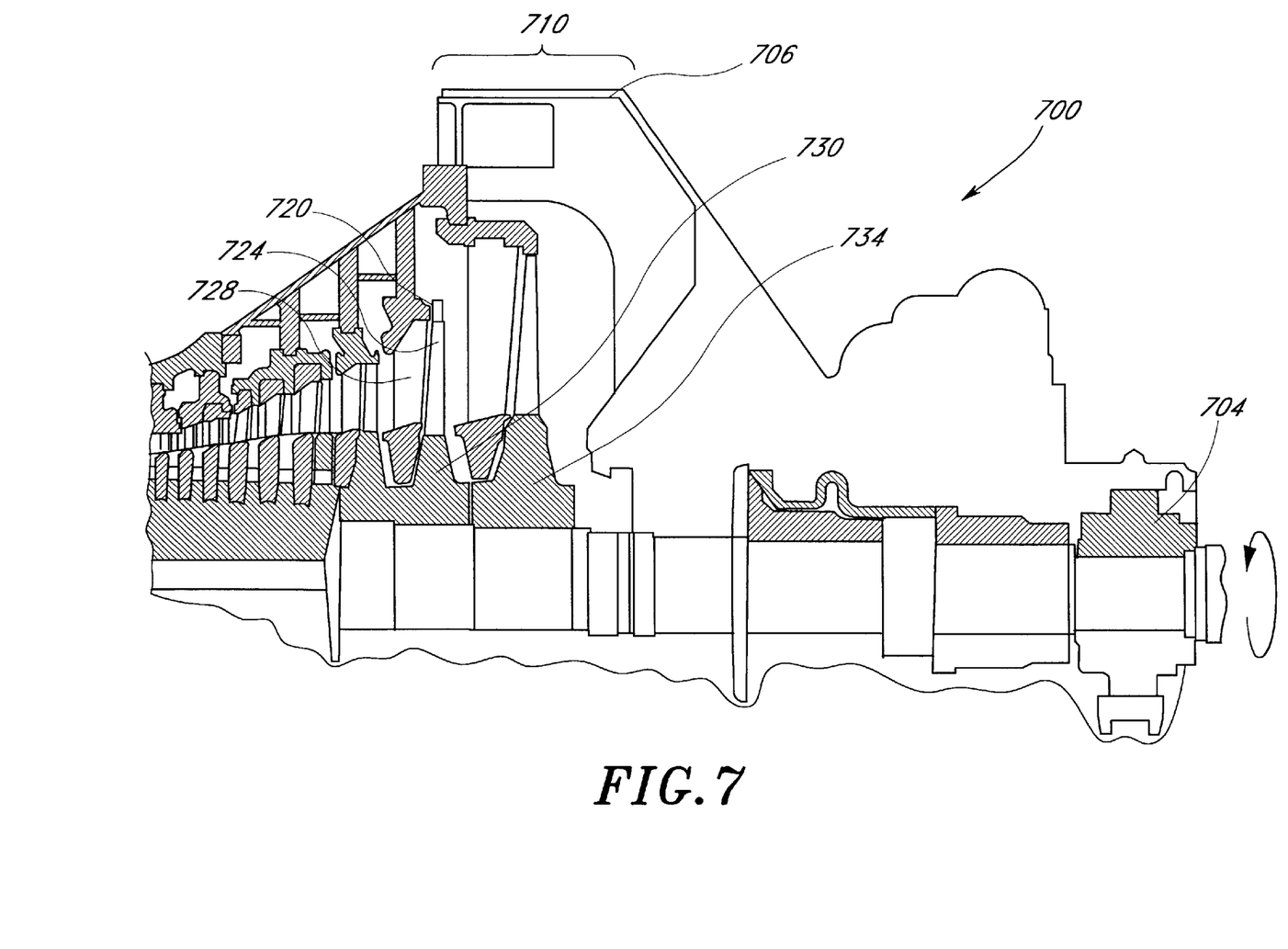
FIG. 7 illustrates a cross section of a low pressure cylinder of a wet steam turbine including a preferred embodiment of the present invention.

FIG. 7 illustrates a cross section of a low pressure cylinder 710 of a wet steam turbine 700 including an alternative embodiment of the present invention. A rotor 704 has numerous disks 730, 734 having blades around their corresponding peripheries. The turbine 700 includes a cylinder or casing 706 and stationary blades 728. A transducer 720, mounted within the casing 706, is spaced apart from the turbine blades. In one preferred embodiment the transducer 720 acts as both a transmitter and receiver. The transducer 720 generates pulses of ultrasonic energy, which are radiated at blades 724 rotating beneath the transducer 720. The void between the moving blades 724 and the transducer 720 if filled with wet steam. As described above in relation to FIG. 1A, a preferred embodiment of the present invention acts as an ultrasonic stroboscope. However, in the present instance, the wet steam advantageously couples the radiated ultrasonic energy from the transducer 720 to the blade 724 and also couples the return signal from the blade 724 to the transducer 720.

Figure 1B:
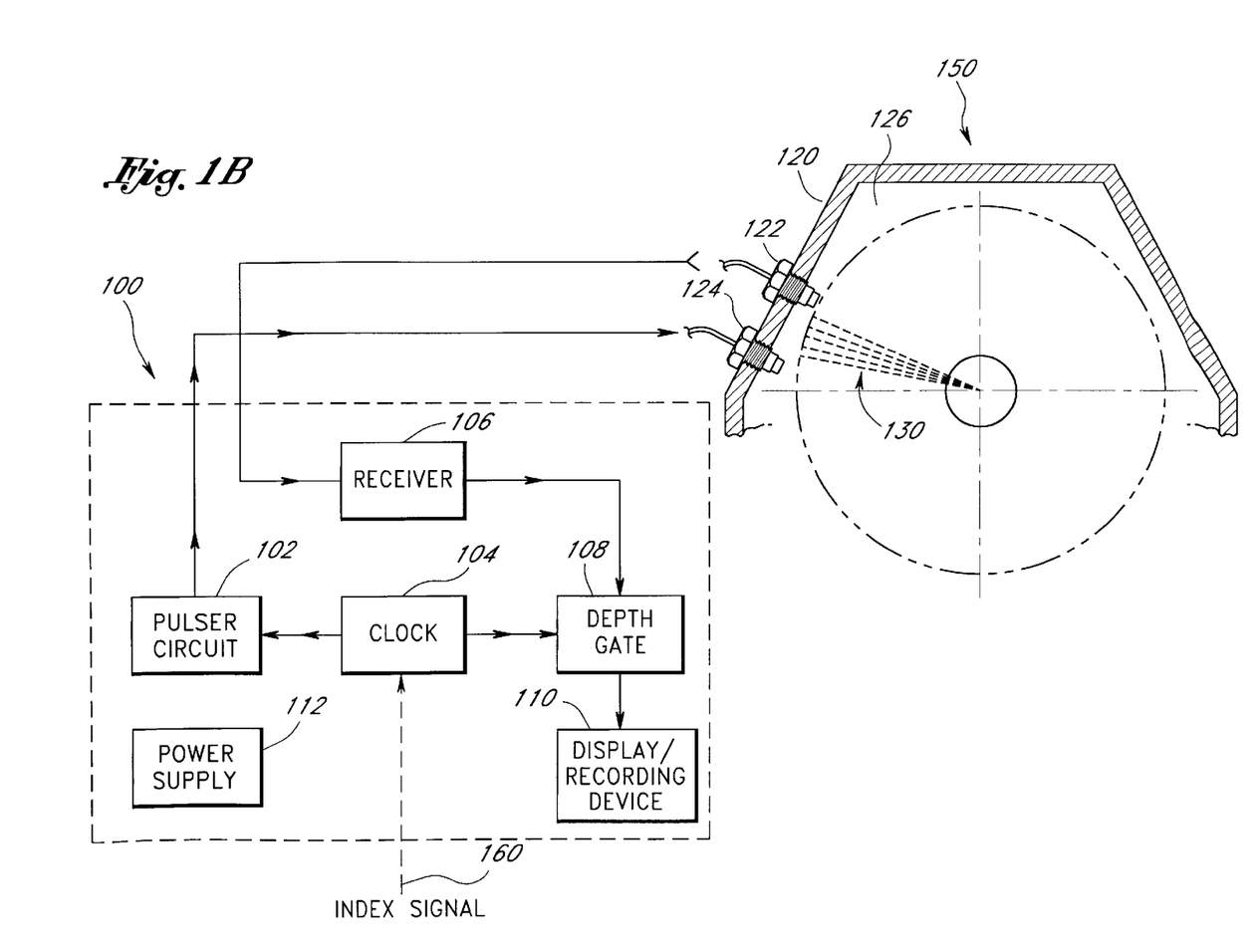
FIG. 1B illustrates an alternative preferred embodiment of the present invention having separate transmitting and receiving transducers.

FIG. 1B illustrates another preferred embodiment of the present invention, including pulse generation/receiver circuitry 100. Rather than have each transducer act as both transmitter and receiver, as described above, separate transducers 124, 122 are used to correspondingly transmit ultrasonic pulses and receive reflected echo returns.

The pulse generation/receiver circuit 100 includes a clock device 104. The clock device 104 generates trigger pulses at regular intervals. An index signal 160 from a turbine 150 may optionally be used to synchronize the clock to the turbine rotation frequency, as discussed above. The trigger pulses are communicated to a pulser circuit 102 and a depth gate 108. The pulser circuit 102 is connected in turn to the transmitting transducer 124. In the illustrated example, the transducer 124 is mounted through a casing 120 of a turbine 150. The transmitting transducer 124 is directed at a rotating object being inspected, such as a turbine blade 130. The receiving transducer 122 is likewise mounted through the casing 120, above the transducer 124. The void 126 between the casing 120 and the blade 130 is filled with a medium such as, by way of example, steam or a liquid. The receiving transducer 122 senses echo returns. The receiving transducer 122 is connected to a receiver 106, which is in turn connected to the depth gate 108. The depth gate 108 is connected to a user interface, such as display and/or a recording device 110. By way of example, the display may be an oscilloscope or a monitor. The recording device may be a plotter, a printer, or a memory storage device such as a semiconductor, optical, or magnetic storage element. As discussed below, the display/recording device 110 provides information related to the echo returns to either a human or a computerized operator. A power supply 112 provides proper operating voltages and currents to the remainder of the pulse generation/receiver circuitry 100.

The operation of the preferred embodiment illustrated in FIG. 1B will now be described. The clock device 104 triggers the pulser circuit 102 at regular intervals. The frequency of the intervals is substantially related to the frequency of rotation of the blade 130. In addition, the clock device 104 sends a timing signal to the depth gate 108. The timing signal sent to the depth gate 108 and the trigger sent to the pulser circuit 102 may be the same signal.

The pulser circuit 102 provides repeating pulses of high-frequency alternating voltage to the transmitting transducer 124. The frequency of the voltage pulses is related to the trigger frequency. The transmitting transducer 124 converts the pulses of alternating voltage into pulses of mechanical vibration having substantially the same frequency as the alternating voltage. In the preferred embodiment, the mechanical vibration in turn produces ultrasonic audio pulses at frequencies substantially between 5 MHz and 15 MHz by way of example.

The audio pulses are directed at the blade 130 and travel through the blade 130 by wave motion. The most significant wave motion is typically longitudinal. However, other wave types, such as surface or traverse waves may occur as well. Surface waves, which do not penetrate deeply, are typically most useful for inspecting the area immediately beneath the surface of the object being inspected. Longitudinal waves are often better than surface waves for inspecting interior portions of an object, while, by contrast, surfaces waves are better at following contoured surfaces.

As discussed above, when an audio pulse encounters a discontinuity, such as a crack, an inclusion, or other type of flaw, at least a portion of the pulse energy is reflected and travels back through the blade 130. However, during the travel time required for the ultrasonic pulse to travel from the transmitting transducer 124 to the discontinuity in the blade 130, and the travel time required for the reflected pulse energy to travel back through the blade 130, the blade 130 has rotated in a clockwise direction away from the transmitting transducer 124. Hence, taking into account the rotation of the blade 130, the receiving transducer 122 is preferably spaced apart from the transmitting transducer 124 so that at least a portion of the reflected energy will strike the receiving transducer 122.

The receiving transducer 122 converts the received reflected energy into an electrical signal which is the provided to the receiver 106. The receiver may amplify and process the transducer signal. The processed transducer signal is provided to the depth gate, which, as described below, may filter out echo returns which are not of interest.

The depth gate 108 is a time-measuring device used to track the timing differential between transmitted pulses and received reflections. The depth gate 108 advantageously allows those return signals which are received within a selected window of time following the transmitted pulse to be displayed or stored. This feature is useful in excluding unwanted echo returns from being displayed or stored. When an ultrasonic pulse is directed at a test piece, such as a turbine blade, multiple echoes returns may result. For example, the first echo ("a front reflection") may result from the pulse striking the outer surface of the test piece. A second echo may result from the pulse striking a crack within the test piece. A third echo ("a back reflection") may result from the pulse striking the rear surface of the test piece.

In one preferred embodiment, the depth gate 108 is set so that front reflections and back reflections are narrowly excluded from the display. Thus, the principal returns which are displayed or recorded are advantageously the result of echoes which originate within the test piece due to internal flaws. By contrast, echoes resulting from reflections off the front and the back of the test piece are excluded. Furthermore, the depth gate 108 may be adjusted to select an even narrower window so that only echo returns from a thin "slice" of the test piece at a selected depth will be displayed. In another embodiment, the window may be widened if the operator wants to receive all echo returns.

The depth gate 108 provides the filtered return signal to the display and/or recording device 110 for evaluation by either an operator or a computerized analysis system. Thus, the described system acts like an audio x-ray, allowing the internal structure of the moving test piece to be inspected. Furthermore, in another embodiment, the return signal may be compared to a reference return signal from an earlier inspection, such as inspection of the turbine performed when the turbine was new, to determine if any changes have taken place.

Figure 2:
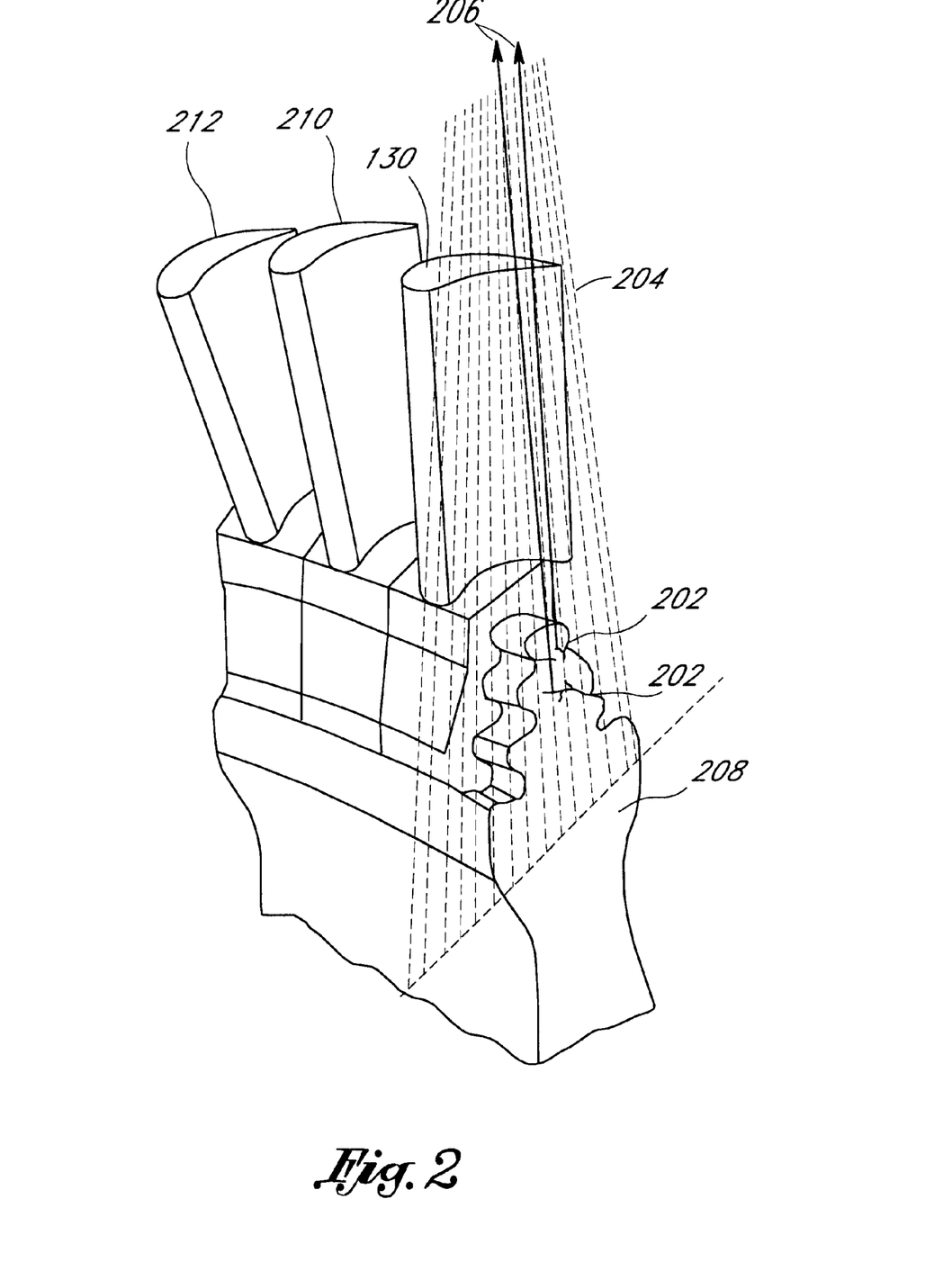
FIG. 2 illustrates an enlarged cutaway of a turbine disk.

FIG. 2 illustrates a cutaway of the turbine disk from FIG. 1B, including the blade 130 mounted on a turbine disc rim 208. Pulsed sound waves 204 are synchronized with and directed at the rotating turbine blade 130. When the sound waves 204 strike discontinuities, such as cracks 202, reflected energy 206 travels back through the blade 130 to the receiving transducer (not shown). The reflected energy may then be detected and analyzed as described above. Sets of ultrasonic pulses are repeatedly transmitted each time the blade 130 passes beneath the transmitting transducer, so that the blade 130 appears acoustically stationary or static.

To inspect another blade, such as a blade 210 or a blade 212, the start time of the next pulse set is varied so that the pulsed sound waves 204 will strike the selected blade, rather than the blade 130.

The selected blade may be identified using signature analysis, wherein the return signal is compared to a reference return signal for that blade taken earlier. Alternatively, the operator may just select a blade at random, inspect that blade, and then simply sequence through each blade.

Figure 3:
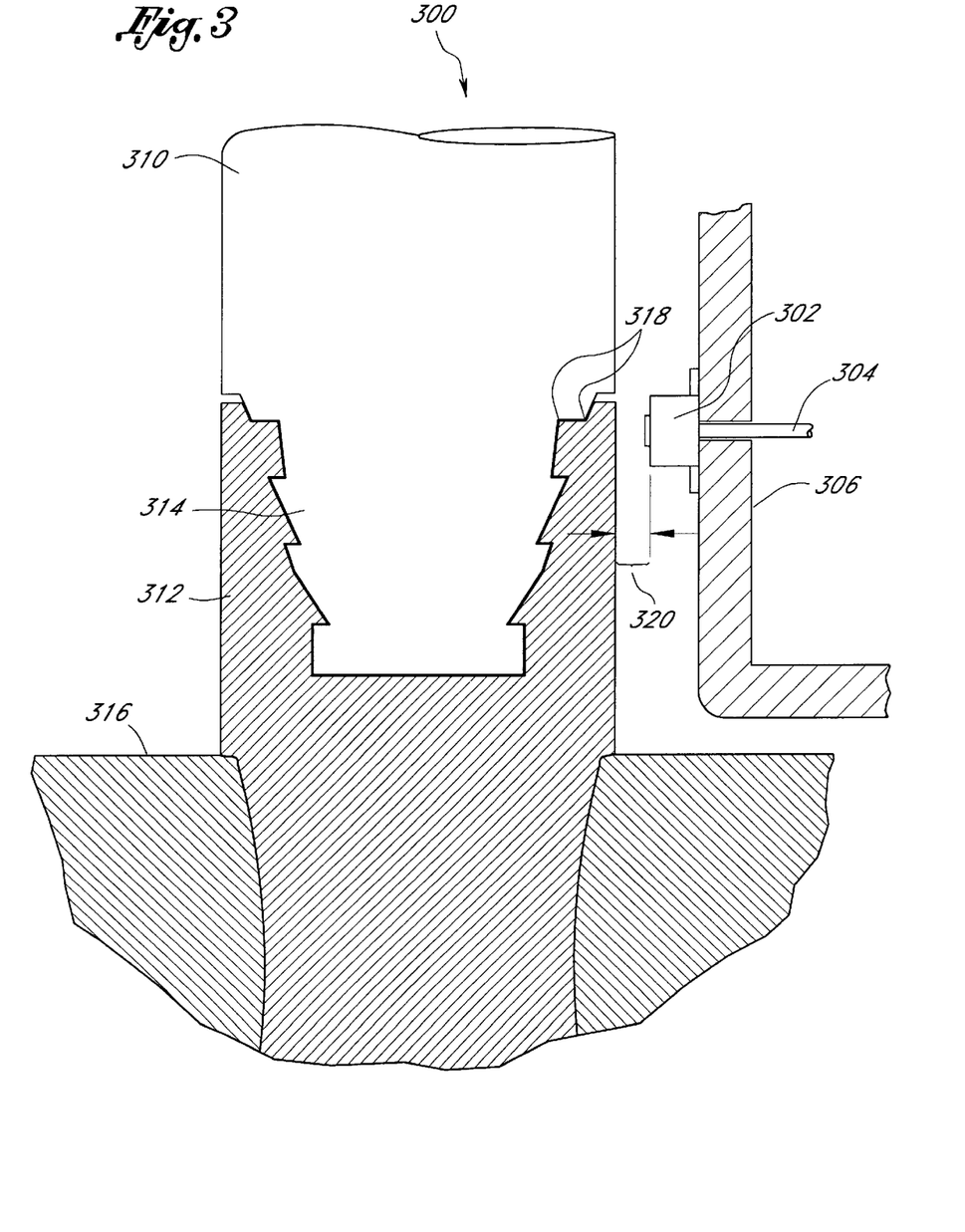
FIG. 3 illustrates another preferred embodiment of the present invention having a transduced mounted orthogonally to a turbine blade root.

FIG. 3 illustrates another preferred embodiment of the present invention which has a transmitting/receiving transducer 302 mounted orthogonally to a root portion 314 of a turbine blade 310. A signal bus 304 couples the transducer to a pulse generation circuit and/or to a receiver (not shown). The blade root portion 314 is affixed to a turbine disk 312, which in turn is mounted to a turbine shaft 316. The transducer 302 is mounted through a casing wall 306 so that it radiates energy at right angles to the rotation of the blade 310. This technique is useful when it is desirable to focus an inspection on an area closer to the side of the blade 310 rather than the top of the blade 310. Mounting the transducer closer to the area of interest results in less attenuation of the transmitted energy and the corresponding echo return. Thus, by mounting the transducer 302 close to the interface of the blade root 314 and the turbine disk 312, inspection of flaws 318 which commonly occur at such interface is greatly enhanced. The method for inspection is similar to that discussed above in relation to FIG. 1B.

FIGS. 4A–4D illustrate idealized anticipated ultrasonic signal returns caused by a variety of flaws. It is understood that actual signal returns would include such artifacts as noise and distortion. For all of FIGS. 4A–4D, the depth gate window has been opened sufficiently wide so that both the front reflection and the back reflection are shown. The vertical axis represents the amplitude of the return signal while the horizontal axis represents the relative time of the return.

Figure 4A:
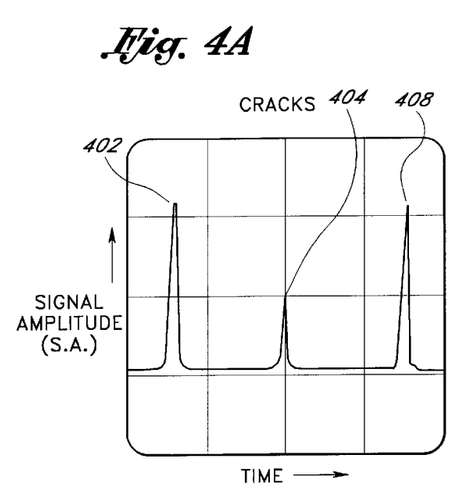
FIG. 4A illustrates the return signal for a crack flaw.

In FIG. 4A, a pulse 402 represents the return from the front surface of a test piece and a pulse 408 represents the return from the back surface of the test piece. A return pulse 404 represents the return from a crack in the test piece. The crack causes a narrow, sharp return pulse, having a lower amplitude that either of the pulses 402, 408. The pulse 404 is characteristic of a crack having a large cross-section in a first direction and a small cross-section in a second direction perpendicular to the first direction.

Figure 4B:
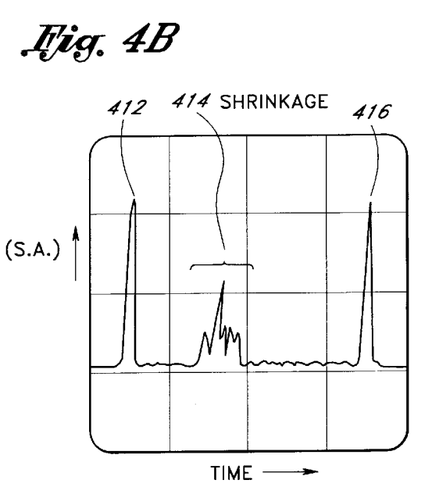
FIG. 4B illustrates the return signal for a shrinkage flaw.

In FIG. 4B, a pulse 412 represents the return from the front surface of a test piece and a pulse 416 represents the return from the back surface of the test piece. A return pulse 414, having a multiple peak pattern, represents the return from a shrinkage flaw in the test piece. The shrinkage flaw typically is an internal rupture occurring in castings due to contraction during cooling.

Figure 4C:
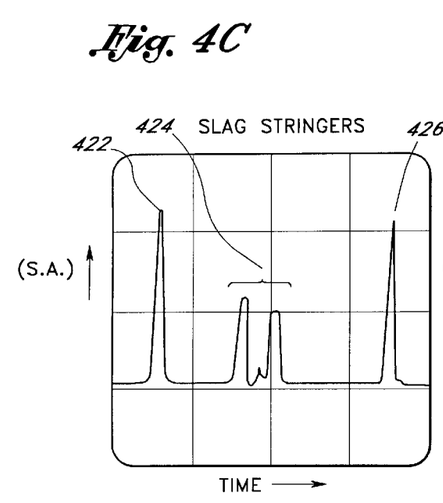
FIG. 4C illustrates the return signal for a slag stringer flaw.

In FIG. 4C, a pulse 422 represents the return from the front surface of a test piece and a pulse 426 represents the return from the back surface of the test piece. A return pulse 424, having two primary peaks, represents the return from a slag stringer in the test piece. The slag stringer typically is an elongated oxidation inclusion.

Figure 4D:
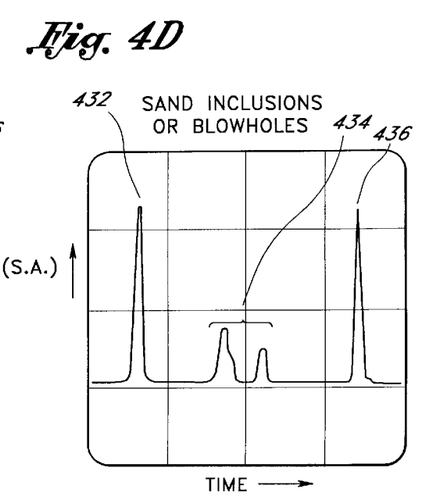
FIG. 4D illustrates the return signal for a sand inclusion flaw.

In FIG. 4D, a pulse 432 represents the return from the front surface of a test piece and a pulse 436 represents the return from the back surface of the test piece. A return pulse 434, having two primary wide peaks, represents the return from a sand inclusion in the test piece. The sand inclusion typically results from sand entrapped in the test piece.

Figure 6:
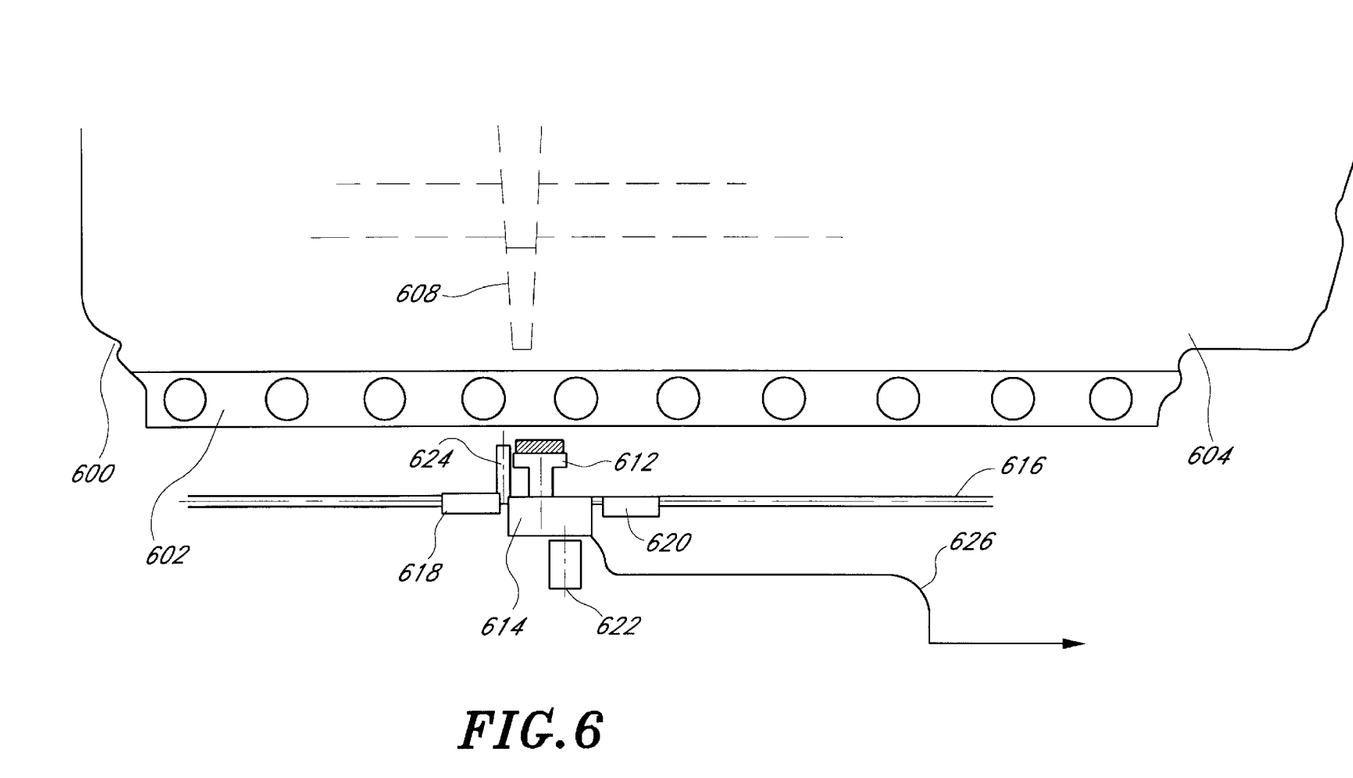
FIG. 6 illustrates a preferred embodiment of a transducer positioning apparatus.

FIG. 6 illustrates an optional preferred embodiment for positioning a transducer 612 externally to a turbine 600. The turbine 600 has a casing formed by bolting an upper case 604 to a lower case (not shown) along a flange 602. The transducer 612 is mounted to a carriage 614. A signal line bus 626 couples the transducer to a pulse generation circuit and/or to a receiver (not shown). The carriage 614 is movably mounted on a guide rail 616 oriented parallel to the flange 602. Two servo motors 618, 620 provide the motor force for moving the transducer 612 along the guide rail 616 so that the transducer 612 may be positioned proximate to a rotor blade 608 or to a turbine stage being inspected. The servo motors 618, 620 may be controlled by either a human or a computerized operator. A third servo motor 622 is used to position the transducer 612 a selected distance from the flange 602. A couplant nozzle 624 may be used to apply a coupling fluid between the transducer 612 and the flange 602, thereby providing better coupling and reduced attenuation of sound waves emitted from the transducer 612.

The apparatus illustrated in FIG. 6 may be used to select a particular rotor stage for inspection using a variety of techniques. For example, the transducer 612 may be moved to predetermined locations for performing an inspection, where each location coincides with the axial position of a turbine stage. The predetermined locations may be physically marked on the guide rail as an aid in positioning the transducer 612 or the may be stored as a coordinate in the computerized operator.

Another method of determining the proper transducer position relative to the turbine stage relies on the fact that echo returns resulting from acoustic pulses striking a moving object are very different from echo returns resulting from acoustic pulses striking a stationary object. The transducer 612 is moved across the rail 616, stopping periodically to determine if the transducer 612 is located in front of a rotating turbine stage. The transducer alternately produces repeating ultrasonic pulses at a repetition frequency equal to the turbine rotation, 60 Hz by way of example, and at a repetition frequency less than the rotation frequency, 25 Hz for example. Regardless of whether either the 60 Hz ultrasonic pulses or the 25 Hz ultrasonic pulses are radiated and strike a stationary portion of the turbine, such as a stator blade, the echo returns will remain essentially the same. By contrast, when the 25 Hz pulses strike a rotating portion of the rotor, having a rotation frequency of 60 Hz, the echo return will be blurred. However, when the 60 Hz pulses strike the same rotating portion, the return will be stable, and the rotating portion will appear acoustically stationary. Thus, an operator can move the transducer 612 along the guide rail 616, while scanning as described above, and thereby determine the location of all the turbine stages. The stages may then be inspected as previously described.

The present invention, as described above, may be used to inspect a variety of rotating or reciprocating components beyond turbine components. For example, the preferred embodiments described above may be used to inspect rotating mill components, such as rollers and drives, railroad and automotive components, such as axles and wheels, and ship components, such as propellers and shafts.

The embodiments of the ultrasonic tester described herein are exemplary embodiments in accordance with the present invention, and are not intended to limit the scope of the invention. Thus, the breadth and scope of the invention should be defined only in accordance with the following claims and their equivalents.

What is claimed is:

1. A method of inspecting at least one portion of a rotating turbine rotor using an ultrasonic stroboscope, wherein the turbine rotor is mounted in a turbine housing and the inspection is performed while the turbine is operating, said method comprising the steps of:

selecting the rotor component to be inspected;

synchronizing said ultrasonic stroboscope with the rotation of said turbine rotor so that a plurality of emitted ultrasonic pulses from a first transducer are directed towards the selected component at a frequency substantially related to the rotation frequency of said rotor to cause said rotating turbine component to appear acoustically stationary;

receiving at least a first echo of at least one of said plurality of emitted ultrasonic pulses using a second transducer, said first echo resulting from said at least one emitted ultrasonic pulse encountering a discontinuity in said turbine component; and supplying information related to said at least one echo for further analysis.

2. The method according to claim 1, wherein said plurality of ultrasonic pulses are emitted at a repetition frequency substantially equal to a sub-harmonic of the rotation frequency of the turbine rotor.

3. The method according to claim 1, further comprising the steps of:

receiving a second echo of said at least one emitted ultrasonic pulse; and setting a window of a depth gate to filter out at least one of said first and second echoes so that information related to the filtered out echo is not provided for further analysis.

4. The method according to claim 1, wherein said synchronizing step includes sensing an index signal indicating the rotation frequency of said rotor.

5. The method according to claim 1, wherein said first transducer and said second transducer are the same transducer.

6. The method according to claim 1, including the step of mounting said first transducer so that at least a portion of said first transducer protrudes through said housing.

7. The method according to claim 1, including the step of mounting said first transducer outside of said housing.

8. The method according to claim 1, wherein said step of selecting a turbine component step further comprises selecting a turbine blade.

9. An ultrasonic stroboscope for inspecting an object rotating at a first frequency to determine if the rotating object has any defects, said ultrasonic stroboscope comprising:

a first acoustic transducer spaced apart from said rotating object, said first transducer configured to radiate ultrasonic energy at said rotating object at a second frequency, said second frequency substantially related to a sub-harmonic of the first frequency so that the rotating object appears acoustically substantially static;

a second acoustic transducer which senses a reflection of said ultrasonic energy from a defect in said rotating object and translates the sensed reflection into at least one reflection signal; and a user interface coupled to receive said reflection signal.

10. The ultrasonic stroboscope according to claim 9, wherein said ultrasonic stroboscope further comprises a depth gate coupled between said reflection signal and said user interface, wherein said depth gate filters out portions of said reflection signal using a timing window.

11. The ultrasonic stroboscope according to claim 10, further comprising an index signal related to the rotation of the rotating object, wherein said index signal synchronizes the radiation of ultrasonic energy with the rotation of the rotating object.

12. A method of inspecting at least one portion of a rotating test piece using an acoustic stroboscope, said method comprising the steps of:

radiating a plurality of sound waves at the test piece using a first acoustic transducer;

synchronizing the radiation of said sound waves with the frequency of rotation of the test piece to cause said rotating test piece to appear acoustically substantially motionless;

receiving at least a first echo of at least one of said sound waves using a second acoustic transducer, said first echo resulting from at least one of said sound waves encountering a discontinuity in the test piece; and providing data related to said at least one echo for further analysis.

13. The method according to claim 12, further comprising the steps of:

moving said first transducer along an axis parallel to an axis of rotation of said test piece;

transmitting said sound waves at a non-integer multiple of the rotation frequency of the test piece;

analyzing echoes of said sound waves to determine when said first transducer is proximate to the test piece; and inspecting the test piece.

14. The method according to claim 12, wherein said sound waves are radiated at a substantially sub-harmonic frequency of the test piece rotation frequency.

15. The method according to claim 12, wherein said first acoustic transducer and said second acoustic transducer are the same transducer.

16. The method according to claim 12, further comprising the step of receiving an echo resulting from said sound waves striking a defect.

17. The method according to claim 12, further comprising the step of receiving an echo resulting from said sound waves striking an inclusion.

18. The method according to claim 12, further comprising the step of receiving an echo resulting from said sound waves encountering a crack.

19. An acoustic stroboscope for inspecting an object rotating at a first frequency, said acoustic stroboscope comprising:

means for directing acoustic energy at a second frequency substantially related to the first frequency so that at least a portion of the rotating object appears acoustically substantially stationary;

means for sensing at least one echo of said acoustic energy, said echo resulting from said acoustic energy impinging on a discontinuity in the rotating object; and means for providing the sensed echo for analysis.

20. The acoustic stroboscope according to claim 19, wherein said acoustic energy is ultrasonic.

21. A method of inspecting a rotating element using an acoustic stroboscope radiating acoustic energy at the rotating element, said method comprising the steps of:

setting a repetition frequency of the radiated acoustic energy so that the frequency of rotation of the rotating element is approximately equal to a multiple of the repetition frequency;

synchronizing the radiated acoustic energy to highlight at least a portion of the rotating element; and receiving at least a first return resulting from the acoustic energy encountering a discontinuity in the test piece.

22. The method according to claim 21, wherein said step of setting a repetition frequency comprises the step of setting the repetition frequency equal to a sub-harmonic of the frequency of rotation of the rotating element.

23. An acoustic stroboscope for inspecting a test piece rotating at a first frequency, said acoustic stroboscope comprising:

an acoustic transducer which radiates acoustic energy at the rotating test piece at a second frequency, said second frequency equal to a multiple of the first frequency;

a receiver which senses a return resulting from said acoustic energy impinging on a discontinuity of said test piece; and a signal coupled to said receiver to provide information relating to the return for analysis.

24. The acoustic stroboscope according to claim 23, wherein said second frequency is equal to said first frequency.

25. The acoustic stroboscope according to claim 23, wherein said second frequency is a sub-harmonic of said first frequency.

* * * * *